United States Patent [19]
Switzer et al.

[11] 4,016,253
[45] Apr. 5, 1977

[54] VACCINE FOR IMMUNIZATION OF SWINE AGAINST *BORDETELLA BRONCHISEPTICA* INFECTION AND METHOD OF USE

[75] Inventors: William P. Switzer; Daniel O. Farrington, both of Ames, Iowa

[73] Assignee: Iowa State University Research Foundation, Inc., Ames, Iowa

[22] Filed: Mar. 29, 1976

[21] Appl. No.: 671,359

Related U.S. Application Data

[63] Continuation-in-part of Ser. No. 564,546, April 2, 1975, abandoned.

[52] U.S. Cl. .................................................. 424/92
[51] Int. Cl.$^2$ ........................................ A61K 39/02
[58] Field of Search ..................................... 424/92

[56] References Cited

OTHER PUBLICATIONS

Farrington D. O. et al., "Resistance to *Bordetella rhinitis*", pp. 44–52 Proceedings, Geo. A. Young Conference on Advances in Swine Repopulation and the Thirteenth Annual Nebraska SPF Conference, Lincoln, Nebraska, July 23–24, 1973.

Harris D. L. et al., Amer. J. Vet. Res. 33(10):1975–1984, Oct. 1972, "Immunization of Pigs Against *Bordetella bronchiseptica* Infection by Parenteral Vaccination".

Harris, D. L. et al., Amer. J. Vet. Res. 30:1161–1166, July 1969, "Nasal and Tracheal Resistance of Swine Against Re-infection by *Bordetella bronchiseptica*".

*Primary Examiner*—Shep K. Rose
*Attorney, Agent, or Firm*—Tilton, Fallon, Lungmus, Chestnut & Hill

[57] ABSTRACT

A strain of *Bordetella bronchiseptica* (ATCC No. 31123) is employed in the form of killed whole cells for parenteral administration to swine or other animals subject to *Bordetella bronchiseptica* infection. Swine can be effectively protected against development of the turbinate atrophy associated with *Bordetella bronchiseptica* infection by parenterally administering to young pigs from 1 to 3 doses of a vaccine containing from $10^9$ to $10^{11}$ cells of said strain. The vaccine can also be administered to breeding sows prior to farrowing for at least partial protection of the offspring.

14 Claims, No Drawings

VACCINE FOR IMMUNIZATION OF SWINE AGAINST *BORDETELLA BRONCHISEPTICA* INFECTION AND METHOD OF USE

CROSS-REFERENCE

This application is a continuation-in-part of co-pending application Ser. No. 564,546, filed Apr. 2, 1975, now abandoned. The benefit of the earlier filing date of said application Ser. No. 564,546 is claimed for this application pursuant to 35 U.S.C. 120.

BACKGROUND AND PRIOR ART

*Bordetella bronchiseptica* has been established as the principal cause of the widespread disease in swine commonly referred to as "turbinate atrophy", because, following the primary infection, the nasal turbinate bones frequently undergo serious deterioration. See *Canad. J. Comp. Med.*, 31, 53–57 (1967), and literature references cited therein. *Bordetella bronchiseptica* bacteria can persist in the nasal cavities, leading to infection of the susceptible offspring of breeding sows.

Baby pigs become infected with *B. bronchiseptica* early in life (under 4 weeks of age) which makes the problem of effective protection particularly difficult, since the immunity system of very young pigs does not respond satisfactorily to vaccines. For effective antibody production, vaccines are usually administered to pigs at an age of about 6 to 8 weeks. By that age, however, if the pigs have become infected with *B. bronchiseptica* damage to the turbinate bones may well occur, even though the pigs become immunized to the infection.

The first treatment proven to be of value in reducing the incidence of infection of young pigs was the administration of a sulfonamide therapeutic agent, such as sulfamethazine or sulfaethoxypyridazine, in the rations fed to the breeding herds. This method was reported in the literature and patented by Dr. William P. Switzer: *Vet. Med.*, 58, 571–575 (1963); and U.S. Pat. No. 3,336,190. However, the effectiveness of sulfonamide therapy in eliminating *Bordetella bronchiseptica* infection has been limited by development of sulfonamide-resistant strains of the organism. For example, a study in 1967 found that isolates of *B. bronchiseptica* recovered from 80% of the herds inspected were resistant to sulfonamide. *Am. J. Vet. Res.*, 30, 1621–1624 (Sept., 1969). This data emphasized the recognized need for additional drugs, or, in particular, effective immunizing agents. Prior to the present invention, however, no other preventative treatment suitable for use in the commercial raising of swine has been developed.

It was found that the introduction of live cells of a low-virulence strain of *B. bronchiseptica* into the nasal cavities of non-immune swine would cause a relatively mild infection, and that thereafter the swine would be immune to further infection, including infection by more virulent strains of the organism. See *J. Vet. Res.*, 30, 1161–1166 (July, 1969). One such low virulent strain, which was not publicly available, was identified by the private code designation of "Strain D-1". This is the same strain used for preparing the killed whole cell parenteral vaccine of the present invention. However, in prior work, live cells of the Strain D-1 were found to persist in the nasal cavities of recovered swine. Therefore Strain D-1 was ruled out as a live whole cell intranasal vaccine. Moreover, no other strain of *B. bronchiseptica* was known which would produce immunity, and thereafter be self-clearing from the nasal passages of the immunized swine.

Attempts were also made to develop a vaccine from killed cells of *B. bronchiseptica* which would induce immunity by parenteral administration. One of the first such experimental vaccines was prepared from a virulent strain of *B. bronchiseptica* (identified as "Strain B"). But this whole cell-vaccine failed to induce resistance to nasal infection as reported by Harris, D. L., and Switzer, W. P.: *Am. J. Vet. Res.*, 30, 1161–1166 (July, 1969). Because of the failure of such whole-cell parenteral vaccines, Harris and Switzer postulated that "exposure of the pig to the internal antigens of *B. bronchiseptica* may be necessary for the production of resistance against nasal infection." *Am. J. Vet. Res.*, 33, 1972, at 1981–1982 (Oct., 1972). This theory proved incorrect. Vaccines prepared from disrupted cells (sonicated) of *B. bronchiseptica*, Strain D-1, failed to prevent *B. bronchiseptica* infection, but induced an accelerated clearance by 40 days post challenge (*A.J. Vet. Res.*, 33, 1972, at 1979 and 1981). It was concluded that the type of resistance induced by a parenteral vaccine containing the liberated antigens of killed cells was different than the immunity of swine which had recovered from intranasal infection with live *B. bronchiseptica*. The goal of effective immunization against the infection remained to be achieved, and no answer to this baffling problem was apparent.

The state of art was summarized by D. O. Farrington and W. P. Switzer in a paper entitled "Resistance to Bordetella Rhinitis," *Proceedings the George A. Young Conference on Advances in Swine Repopulation and the Thirteenth Annual Nebraska SPF Conference*, Lincoln, Nebraska, July 23–24, 1973, pp. 44–52. It was reported that parenteral immunization of swine with *B. bronchiseptica* bacterins is known to accelerate nasal clearance of *B. bronchiseptica* infections, and that development of the gross lesions associated with atrophic rhinitis appears to be significantly inhibited in suitably immunized swine. Trials with experimental *B. bronchiseptica* bacterins as summarized in Table 1 show positive results. However, it was concluded: "Many unanswered questions remain before the development of a practical immunizing agent against Bordetella rhinitis becomes a reality."

DESCRIPTION OF THE INVENTION

As indicated above, *Bordetella bronchiseptica* infection is the primary cause of atrophic rhinitis. Frequently, in the aftermath of the infection, the turbinate bones undergo serious atrophy. In the colonization of the nasal passages by the Bordetella organisms, they penetrate the mucus layer and anchor themselves in colonies to the epithelial cells. During the infection, toxic substances are produced, which reach the underlying tissue, and in particular, the bone-forming cells of the nasal turbinate. Such toxic substances are believed to produce the lesions causing turbinate atrophy. The present invention provides a means for effectively immunizing against the toxic substances which cause turbinate atrophy without preventing the primary *B. bronchiseptica* infection. More specifically, in the work leading to the present invention, it was discovered that a killed whole cell vaccine could be prepared from a strain of *B. bronchiseptica* identified herein by ATCC No. 31124; which, when administered in a critical dosage, was capable of effectively protecting swine against development of the turbinate atrophy. In addition, although the vaccinated swine are not immune to infection, an accelerated clearance of the B. bronchiseptica infection is usually obtained. However, the principal new result of the present invention is that it immunizes against turbinate lesions accompanying B. bronchiseptica infection. This is important since such lesions and the resulting nasal bone deterioration are a major cause of economic loss to swine raisers. Because of the prevalence of Bordetella bronchiseptica organisms in breeding herds, and the great practical difficulty of maintaining breeding herds free of B. bronchiseptica it is extremely difficult to avoid infection of young pigs at a susceptible age.

Further important details with respect to the preparation of vaccines in dosage form in accordance with the present invention, and the method of using such vaccines, are disclosed below. Killed whole cell parenteral bacterins prepared from Strain ATCC No. 31124 have been found to be effective in preventing turbinate atrophy and in reducing the duration of B. bronchiseptica infection. Furthermore, it has been found that baby pigs at ages under 4 weeks respond satisfactorily to the bacterins of this invention. The present invention therefore provides a means for providing baby pigs with antibody protection against turbinate atrophy before they have had an opportunity to become infected with resulting nasal bone lesions.

Prior to the filing of the present application, there was placed on deposit with the American Type Culture Collection, Rockville, Md., viable samples of the strain of B. bronchiseptica, which can be used as seed cultures for producing the vaccine of the present invention. The deposited identical samples, earlier identified by the private code designation Strain D-1, have been assigned ATCC No. 31124, which will therefore be used as the identifying reference in this specification and appended claims. The available taxonomic description of B. bronchiseptica Strain ATCC No. 31124 is:

Taxonomic Description

ATCC No. 31124 was recovered from the nasal and tracheal exudate of a young mongrel pup that had clinical signs of canine distemper. This strain was subsequently determined to be avirulent for swine, and to have the following identifying characteristics:

1. Small gram-negative rod.
 2. Aerobic.
 3. Colony approximately 1 mm in diameter after incubation on 5% horse blood agar for 48 hours at 37° C.
 4. Colony circular, low convex, entire, opaque, smooth, homogenous with undulate margin on 5% horse blood agar.
 5. Alkalinization of lactose broth in 18–24 hours without gas formation.
 6. Alkalinization of dextrose broth in 18–24 hours without gas formation.
 7. Urease positive within 2–12 hours.
 8. Citrate positive within 12–24 hours.
 9. Nitrate positive.
 10. Alkalinization of litmus milk within 48 hours.
 11. Motile by means of peritrichous flagella.
 12. Grows on MacConkeys agar in the presence of bile salts.
 13. Sensitive to sulfamethazine at 5 mg/ml level on disc assay.
 14. Resistant to 0.02 mg/ml furaltadone (NF-260).
 15. Hemagglutination positive (2.8% suspension of sheep red blood cells).
 16. Hemolytic on 5% horse blood agar after incubation at 37° C. for 24 hours.
 17. Non spore forming.
 18. Catalase positive.
 19. Oxidase positive.
 20. Indole negative.
 21. Hydrogen sulfide negative.
 22. Gelatin liquafaction negative.

In preparing the vaccine of the present invention, viable cells of B. bronchiseptica strain ATCC No. 31124, which may have been subjected to freeze-drying for preservation, are introduced into a suitable culture medium, which is then incubated at a temperature favoring the growth of the organism. In general, published procedures for culturing B. bronchiseptica organisms can be employed. See, for example, Am. J. Vet. Res., 30, 1161, 1162 (1969); and Am. J. Vet. Res., 33, 975, at 1976 (1972). More specifically, tryptose phosphate broth (TPB) may be used for propagation of the organism. One suitable source of such a TPB medium is Difco Laboratories, Inc., Detroit, Mich. Other useable culture mediums include: Bordet-Gengou Agar (Difco), Brain-Heart Infusion Broth (Difco), tryptone soya broth (Oxoid Limited, London, England). Propagation temperatures of 36° to 38° C. are favorable. More detailed propagation directions are set in the following examples.

After propagation, the culture of ATCC No. 31124 is killed without disruption of the cell walls. Suitable killing agents include a final concentration of 0.2% formaldehyde of or 1:10,000 thimerosal (sodium ethylmercurithiosalicylate). A preferred procedure is to add formalin, a 37% aqueous solution of formaldehyde. Final formaldehyde concentrations of 0.1 to 0.2% are sufficient for complete inactivation where the cells are held for 24 hours at room temperature (20°–25° C.). After killing, the intact cells can be stored under refrigeration (viz., at 4° C.). Preferred concentrations of the bacteria range from about $10^9$ to $10^{11}$ cells per milliliter, such as substantially $10^{10}$ cells per milliliter. Such killed cell concentrates are well suited for preparing vaccines in the dosage form for practicing the present invention.

As is known to the art of preparing parenteral vaccines, a suitable adjuvant can be mixed with the killed cells in preparing the vaccine for administration. An effective amount of an adjuvant mixed with the killed cells can increase antibody production in the vaccinated animals. For meat-producing animals, such as swine, it is desirable that the adjuvant be absorbable, whether injected subcutaneously or intramuscularly. It is therefore desirable, at least for use in the United States, to employ an adjuvant which is approved by the U.S. Department of Agriculture, Veterinary Biologics Division, for administration to meat-producing animals. Aluminum hydroxide (alumina cream) has value as an adjuvant in the vaccines of the present invention, and is approved for use in meat-producing animals. The use of this adjuvant is illustrated in the examples. Another useable adjuvant is one prepared as described in U.S. Pat. No. 3,149,036. A commercial form of this adjuvant is sold by Merck & Co., Inc., Rahway, N.J., as Merck Adjuvant 65. The preparation and use of this adjuvant is also described in the examples.

The vaccine of this invention in parenterally injectable dose form consists essentially of the adjuvant in admixture with from about $10^9$ to $10^{11}$ killed whole cells of said strain ATCC No. 31124. The preferred vaccine dose contains from 5 to 15 × $10^9$ cells of said strain. Such vaccine doses are particularly suitable for immunizing swine against development of turbinate atrophy. The total dose volume of the vaccine will include the cell volume plus the volume of the injectable absorbable adjuvant. The dose volume will usually be more than 0.5 milliliters and less than 3.0 milliliters, but should be of sufficient size to include an effective amount of the adjuvant. Dose volumes of from 0.8 to 2.5 milliliters are particularly suitable for intramuscular or subcutaneous administration. In one preferred preparation, from 10 to 15 × $10^9$ cells are present, and the total dose volume is from 1.8 to 2.2 milliliters.

The vaccine of this invention can also be used for protecting the offspring of a pregnant sow against the development of turbinate atrophy. For example, at least one dose of the vaccine containing from $10^9$ to $10^{11}$ killed whole cells of Strain ATCC No. 31124 is parenterally administered to the pregnant sow not less than 14 days prior to farrowing. In a preferred procedure, from two to three doses of the vaccine are administered to the pregnant sow at intervals of not less than 5 days between doses. For example, two injections of the vaccine may be given, the first one approximately 28 days before farrowing, and the second one approximately 14 days before farrowing.

Procedures for practicing the present invention in its various embodiments are illustrated by the following examples.

EXAMPLE I

Bacterins for use in practicing the present invention can be produced by the following procedure:
1. Lyophilized D-1 Strain (ATCC No. 31124) is removed from storage at −20° C. and incubated overnight at 37° C. in TPB (Tryptose phosphate broth).
2. Transfer TPB culture into desired quantity of TPB in a suitable container.
3. Aerobically incubate for 24 to 48 hours.
4. Purity check and determination of colony forming units on 5% horse blood agar.
5. Add formaldehyde, 37% solution (J. T. Baker, Phillipsburg, N.J.) to a final formalin concentration of 1:1000. Mix well.
6. Incubate overnight at room temperature. Mix well. Inactivation and sterility check on 5% horse blood agar.
7. Store at 4° C.

EXAMPLE II

Adjuvants suitable for use in practicing the present invention can be prepared as follows:

Aluminum Hydroxide Adjuvant

1. A suitable amount of aluminum hydroxide compressed gel, eg. 384g., containing about 9.5% $Al_2O_3$ is mixed with deionized water in variable amounts to make a final 20% aluminum hydroxide solution.
2. The final solution will provide approximately 2% $Al_2O_3$.
3. Autoclave sample.
4. Store at room temperature.

Peanut Oil Adjuvant

1. The adjuvant is composed of 85.0% peanut oil, 10.6% mannide monooleate (Arlacel A), and 4.4% aluminum monostearate.
2. A suitable quantity of each ingredient is mixed in the above proportions in a suitable container on a heater-stirrer.
3. The temperature is raised at the rate of 4° C. per minute to 120° C.
4. The mixture is constantly stirred with a glass rod during the heating process.
5. The homogenous material is dispensed into amber bottles and autoclaved.
6. Store at room temperature.

This adjuvant is referred to as Adjuvant 65, and is obtainable from Merck & Co., Inc., Rahway, N.J. (See U.S. Pat. No. 3,149,036.)

EXAMPLE III

Suitable procedures for preparing vaccines using the adjuvants of Example II are set out below.

Preparation of Vaccine with Aluminum Hydroxide Adjuvant

1. Equal volumes of the aluminum hydroxide adjuvant (20% solution) and inactivated TPB D-1 strain broth culture are thoroughly mixed in a suitable container to form the complete vaccine.
2. The vaccine will contain approximately 1% $Al_2O_3$.
3. The final concentration of the vaccine contains approximately $10^{10}$ cells per ml.
4. The vaccine is stored at 4° C. until use in 100 ml. glass, rubber stoppered, sealed, vials.
5. For administration to baby pigs, two ml. of the vaccine would be administered subcutaneously.

Preparation of Vaccine with Peanut Oil Adjuvant

1. Equal volumes of the peanut oil adjuvant and inactivated TPB D-1 strain broth culture are thoroughly emulsified to form the complete vaccine.
2. The final concentration of the vaccine contains approximately $10^{10}$ cells per ml.
3. The vaccine is stored at 4° C. untl use in 100 ml. glass, rubber stoppered, sealed vials.
4. For administration to baby pigs, two ml. of the vaccine would be administered subcutaneously.

EXAMPLE IV

A preferred vaccination procedure for baby pigs is as follows:
1. A two ml. dose of either of the vaccine products of Example III is administered to each pig at 1 week and at 4 weeks of age.
2. The vaccine is injected subcutaneously.

EXAMPLE V

A preferred vaccination procedure for sows prior to farrowing is as follows:
1. A two ml. dose of either of the vaccine products of Example III is administered to each dam at 4 weeks and at 2 weeks prior to farrowing.
2. The vaccine is injected subcutaneously.
3. Females with high levels of humoral antibody against B. bronchiseptica can be expected to transfer high levels of anti-Bordetella bronchiseptica antibody via the colostrum to the susceptible young pigs.

We claim:

1. A vaccine in parenterally injectable dose form for administration to animals subject to *Bordetella bronchiseptica* infection, consisting essentially of an effective adjuvant in admixture with killed whole cells of the strain of *Bordetella bronchiseptica* identified by ATCC No. 31124, said vaccine dose containing from $10^9$ to $10^{11}$ cells of said strain.

2. The vaccine of claim 1 in which said dose contains from 5 to 15 × $10^9$ cells of said strain.

3. A parenteral vaccine in dose form for immunizing swine against development of the turbinate atrophy associated with *Bordetella bronchiseptica* infection, comprising an injectable absorbable adjuvant suitable for parenteral administration to meat-producing animals in admixture with from $10^9$ to $10^{11}$ killed whole cells of the strain of *Bordetella bronchiseptica* identified by ATCC No. 31124.

4. The vaccine of claim 3 in which said dose contains from 5 to 15 × $10^9$ cells of said strain.

5. The vaccine of claim 3 in which said dose has a total volume of more than 0.5 milliliters and less than 3.0 milliliters.

6. The vaccine of claim 4 in which said dose has a total volume of from 0.8 to 2.5 milliliters.

7. A parenteral vaccine in dose form for immunizing swine against development of the turbinate atrophy associated with *Bordetella bronchiseptica* infection, comprising an injectable absorbable adjuvant suitable for parenteral administration to meat-producing animals in admixture with from 10 to 15 × $10^9$ killed whole cells of the strain of *Bordetella bronchiseptica* identified by ATCC No. 31124, said dose having a total volume of from 1.8 to 2.2 milliliters.

8. The method of protecting swine against development of the turbinate atrophy associated with *Bordetella bronchiseptica* infection comprising parenterally administering to pigs at an age of from 2 to 56 days at least one dose of a vaccine characterized by containing from $10^9$ to $10^{11}$ killed whole cells of the strain of *Bordetella bronchiseptica* identified by ATCC No. 31124.

9. The method of claim 8 in which said dose contains from 5 to 15 × $10^9$ cells of said strain.

10. The method of claim 8 in which said dose is administered from 2 to 3 times at intervals of not less than 5 days apart.

11. The method of protecting swine against development of the turbinate atrophy associated with *Bordetella bronchiseptica* infection and accelerating clearance of such infection, comprising parenterally administering to pigs at an age from 5 to 21 days at least one dose of a vaccine characterized by containing from 5 to 15 × $10^9$ cells of the strain of *Bordetella bronchiseptica* identified by ATCC No. 31124.

12. The method of claim 11 in which said dose contains from 10 to 15 × $10^9$ cells and is administered twice at an interval of not less than 1 week between said doses.

13. The method of protecting the offspring of a pregnant sow against development of the turbinate atrophy associated with *Bordetella bronchiseptica* infection, comprising parenterally administering to the pregnant sow not less than 14 days prior to farrowing at least one dose of a vaccine characterized by containing from $10^9$ to $10^{11}$ killed whole cells of the strain of *Bordetella bronchiseptica* identified by ATCC No. 31124.

14. The method of claim 13 in which from 2 to 3 doses of said vaccine are administered to said pregnant sow at intervals of not less than 5 days between doses.

* * * * *

UNITED STATES PATENT OFFICE
CERTIFICATE OF CORRECTION

Patent No. 4,016,253      Dated April 5, 1977

Inventor(s) William P. Switzer and Daniel O. Farrington

It is certified that error appears in the above-identified patent and that said Letters Patent are hereby corrected as shown below:

Title page, under subtitle ABSTRACT, line 2 change "31123" to --31124--.

Signed and Sealed this

Eighteenth Day of September 1979

[SEAL]

Attest:

LUTRELLE F. PARKER

*Attesting Officer*     *Acting Commissioner of Patents and Trademarks*